United States Patent [19]

Handa et al.

[11] Patent Number: 4,964,414

[45] Date of Patent: Oct. 23, 1990

[54] ELECTRODE FOR USE IN IMPLANTING IN A LIVING BODY

[76] Inventors: Yasunobu Handa, 7-4, Arigasaki 3-chome, Matsumoto-shi, Nagano-ken; Nozomu Hoshimiya, 5-3-403-11, Miyanomori Sanjyo 10-chome, Chuo-ku, Sapporo-shi, Hokkaido; Takashi Oda, c/o Nippon Seisen Co., Ltd., 45, Kouraibashi 5-chome, Higashi-ku, Osaka-shi, Osaka-fu; Yoshinori Tanimoto, c/o Nippon Seisen Co., Ltd., 117-1, Ikenomiya 4-chome, Hirakata-shi, Osaka-fu, all of Japan

[21] Appl. No.: 202,812

[22] Filed: Jun. 6, 1988

[30] Foreign Application Priority Data

Aug. 27, 1987 [JP] Japan ................... 62-215882

[51] Int. Cl.$^5$ ............................................. A61N 1/05
[52] U.S. Cl. ..................... 128/784; 128/642
[58] Field of Search ............ 128/784, 642, 692; 174/69, 786, 785

[56] References Cited

U.S. PATENT DOCUMENTS 3,333,045  7/1967  Fisher et al. ................. 128/784
3,854,002  12/1974 Glander et al. ................ 174/69
4,640,983  2/1987  Comte ......................... 128/784

FOREIGN PATENT DOCUMENTS 60-108054  6/1985  Japan.
61-217174  9/1986  Japan.
1257810  12/1971 United Kingdom ............. 174/69

OTHER PUBLICATIONS

A Percutaneous Wire Electrode for Chronic Research Use, C. W. Caldwell et al., IEEE Transactions on Bio. Med. Eng., vol. 22, No. 5, pp. 429-432, (1975).

Primary Examiner—Lee S. Cohen
Assistant Examiner—Scott Getzow

[57] ABSTRACT

The present invention relates to an electrode which is implanted in a living body, and which is used as an electrical stimulation system for the functional training or restoration of paralyzed muscles, and for the measurement of electrical signals of the living body, and the like.

The electrode comprises: a core comprising a plurality of infinitesimal stainless steel wires of over 180 kg/mm$^2$ in tensile strength and under 25 microns in diameter; and a resin coat provided on the surface of the core, made of a resin compatible with the living body. According to one aspect of the invention, the diameter of the electrode is under 0.3 mm; the electrode is provided with a spirally coiled part along its longitudinal direction; the core is stranded in one direction; and the above mentioned coiled part is coiled in the direction opposite to the stranding direction of the core.

6 Claims, 3 Drawing Sheets

ELECTRODE FOR USE IN IMPLANTING IN A LIVING BODY

BACKGROUND OF THE INVENTION

1. Field of the Invention

The present invention relates to an eletrode which can be implanted into a living body for creating an electrical stimulation system. Such a system is used as a method for functional training or restoration of paralyzed muscles, and for the measurement of electrical signals of the living body, etc.

2. Description of the Prior Art

Because of disturbances in the neuromuscular system resulting from cerebrovascular disorders, spinal cord injury, or other injuries, investigations are presently being made to recover the lost function of body strength. Rehabilitation medicine, one side, and on the electrical stimulation (hereinafter referred to as "FES") on the other side are being investigated with the aim toward restoring or helping the disturbance of motor function which is not at all restorable through the mere employment of utensil or operations dependent on electrical stimulation from the outside.

Similarly, in the case of other than the above, sometimes in order to supply the electricity direct to the living body, and sometimes conversely in order to detect electrical signals from nerves and muscles of the living body, there is conducted the implantation of electrodes direct into the living body.

For example, the above-mentioned FES system, has already been proposed in the official gazettes; the Japanese Patent Application Disclosure No. 217174 of 1986 or the Japanese Patent Application Disclosure No. 108054 of 1985. Especially in the latter official gazette, the electode used for this purpose is made up of twisting together carbon fibers or stainless steel fine wires (for example, about 0.2 mm in diameter) coated on their surfaces with a resin.

On the other hand, the inventors, obtained electrodes offered for clinical purposes in accordance with the FES system, made by the A-M system corporation (U.S.A.), and constructed by intertwisting seven solution treated stainless steel wires.

This electrode is a thread-like filament material of about 0.6 mm in diameter, which is formed by coating the surface of the conductor 12 made by twisting together seven pieces of the above-mentioned stainless steel fine wires 11 with a resin 14 with the exception of its one end part 13, as illustrated in FIG. 5. The whole body of the formed electrode is formed with a coil shape.

This electrode 10 is inserted percutaneously into the living body A so that its one end part 13 is located near the nerve 18, and the other end is connected through the plug 15, the lead wire 16, and other elements to the electrical stimulation device 17. The device is so constructed so that an electric current is generated from the end part 13 of the electrode 10 to stimulate the above-mentioned nerve 18. Thus the structure of the FES system is completed. Reference number 19 in the figure is the guiding needle for inserting the electrode 10 into the living body A.

The present inventors examined many electrodes of such type with the result that when the conductor was covered with resin and implanted in the affected part of a living body, the following disadvantageous results attributable to the properties of material of the above-mentioned conductor itself were noted.

That is, in the electrode as disclosed in the above-mentioned official gazette: the Japanese Patent Application Disclosure No. 108054 of 1985, each of stainless steel fine wires contained therein was considerably large, i.e., about 0.2 mm in diameter and has a relatively large rigidity. This gives rise to a problem that the above-mentioned non-covered end portions tend to injure the living body when contacting directly with the nerve or muscle due to expanding/contracting or shifting of the electrodes in the body.

Such an electrode in facet heightens the physical burden of the patient himself due to the insufficiency is the flexibility of the electrode when it is used in such the regions, as the internal ear or the spinal cord which is very sensitive and susceptible to tissue lesion.

In this case, it has been suggested to use some soft wire with the object of making the above-mentioned fine wire soft. However, the use of soft wire makes it difficult to effectively treat the body because the wire readily changes in its form and further, the end part of the electrode tends to shift and deform as mentioned above. On the other hand, the above-mentioned fine wire tends to bread due to the repeated bending fatigue, thereby lowering the property of electrical conductivity.

On the other side, there is also disclosed in the above-mentioned official gazette the use of carbon fiber, however, the carbon fiber is generally inferior in flexibility. Therefore, when taking the problem of breakage into consideration, it is difficult to say that such a fiber may be used with reliability.

SUMMARY OF THE INVENTION

The object of the present invention is to solve the controversial points mentioned above and to provide an electrode which is implanted into a living body which is usable in the treatment of the human body. The electrode is made of hard drawn stainless steel infinitesimal wire (hereinafter referred to as "infinitesimal wire") having a prescribed cross section and identified as the material of the inner conductor (hereinafter referred to as "core") of the electrode. The electrode exhibits strength and flexibility which are both closely akin to the living tissue of the human body in which it is implanted.

According to one aspect of the present invention, the electrode comprises: a core comprising a plurality of infinitesimal stainless steel wires of over 180 kg/mm$^2$ in tensile strength and under 25 microns in diameter. A coating is provided on the surface of the core of resin which is made compatible with the living body.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

A detailed explanation will now be made about the present invention together with an example thereof.

Figure 1:
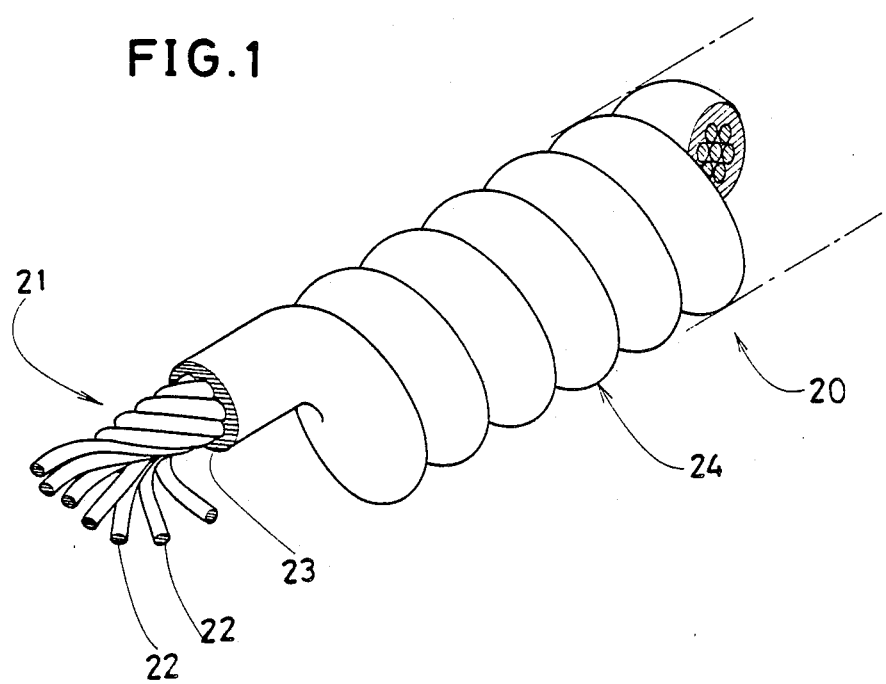
FIG. 1 is an enlarged perspective view showing an embodiment of the present invention.

FIG 1 shows an enlarged perspective view of an electrode 20 containing a core 21 comprising a filamentous material made by putting together (in this example, by intertwisting) a plurality of infinitesimal wires 22. The core is arranged along the longitudinal direction of the electrode in the middle thereof, and furthermore each wire has a substantially round cross section of under 25 microns in diameter, and more preferably 20 to 10 microns in diameter. Further, the electrode is provided on the surface of the core with a resin coat 23 which is compatible with the living body, whereby the infinitesimal wires are integrally embedded therein and the core is electrically isolated. Further, the tensile strength of each infinitesimal wire 22 is set so as to possess a property of over 180 kg/mm².

The inifinitesimal wire 22 of this kind may be selected from steels of various types including, for example, SUS304, 316, 316L which are well known as austenitic stainless steels. However, in particular, the above-mentioned three types of steels are suitable for carrying out the present invention on account of their excellence both in strength and in resistance to corrosion.

Figure 6:
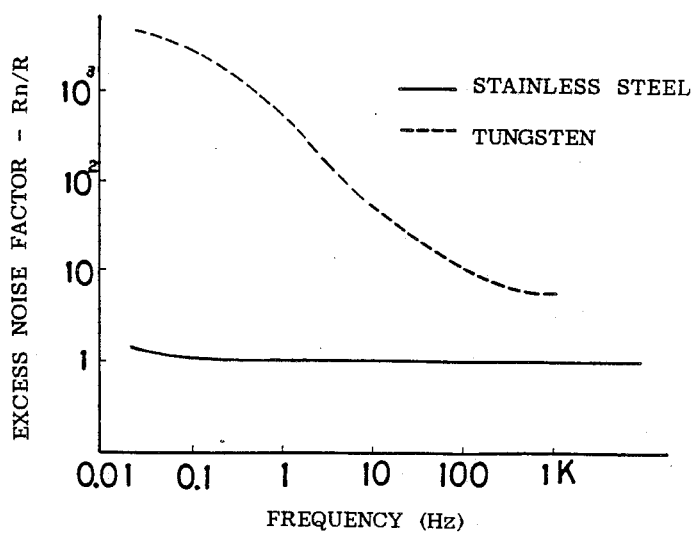
FIG. 6 is a diagram explaining the noise property in the stainless steel infinitesimal wire.

Now turning to the present subject, it has been confirmed by the applicants through experiments conducted during the development of the electrode that, in electrodes of stainless steel, both the equivalent noise resistance Rn thereof and the resistance R of the impedance thereof, when the equivalent circuit of the electrode is indicated as a series circuit of resistance and reactance, correspond well with each other within the limits of, for example, above 1 Hz, whereby the excess noise factor (Rn/R) becomes 1, and excessive noise, other than theoretical thermal noise, does not exist. Thus the electrode material of the present invention is preferable when compared to other materials such as, for example, tungsten or platinum. FIG. 6 represents graphically the above-mentioned facts.

Moreover, the core of the present invention utilizing a plurality of inifinitesimal wires is able to create a total cross sectional area larger than that of a monofilament core, and further provides a much larger surfce area which contacts the living body. Accordingly, the above-mentioned resistance R or the equivalent noise resistance Rn becomes smaller, and also that between the core and the living body also become smaller. The present invention, therefore, provides an excellent electrode having a very low noise property.

The reason why the diameter and tensile strength of the above-mentioned infinitesimal wire 22 is to be set within the limits as mentioned above is based on the recognition that generally stainless steel, even in a soft state, has a high tensile strength of about 50–80 kgf/mm, whereby the holding energy develops a tendency to grow larger with an increase in the diameter and tensile strength of the wire. As a consequence, when taking into consideration both the fitting nature within the living body in the point of strength and the stability of the initial setting form to the shifting of the muscles, the stainless steel used in the electrode is most preferably within the above-mentioned limits and also the above-mentioned noise is small. That is, when the diameter of the infinitesimal stainless steel wires is over 25 microns, the rigidity of the wire itself and that of the core become larger than the living tissue and thus the flexibility of the wire lessens, whereby the problem of injury to the living tissue may take place, as described above. On the contrary, when the diameter of the wire is under 10 microns the strength of the wire becomes small, and it also becomes difficult to produce such very fine wires, and furthermore, the strength of the electrode may be decreased. On the other hand, such hard drawn wires having tensile strengths within the acceptable limit process a fibriform construction wherein one crystal structure extends in the longitudinal direction (i.e. it exists as one crystal in cross section) and the wire itself has both a high elastic limit and a high modulus of elasticity, so that it is also excellent in springyness, thereby providing an electrode of high flexibility. It is possible for the infinitesimal wires used in the invention to prevent the phenomenon of locally repeated bending when in use, and also to stabilize the conductivity by leveling up the uniformity of intertwisting the wires.

The infinitesimal wire 22 having the characteristics of the present invention are obtainable by various die drawing processes presently being used, such as for example, a wire stretching process using a diamond die. In particular, wires obtained by these processes are preferably used in the present invention because they have a smooth surface, and the sliding property among the inifinitesimal wires 22 is heightened. Consequently, it is possible to provide an electrode with excellent flexibility.

It is also possible to provide these infinitesimal wires 22 with improved springness by heat treating them at low temperatures, for example, at temperatures ranging between about 300° and 500° C. before or after combining them together, as occasion demands.

In the present invention, the plurality of wires, for example, about 7–200 pieces of the above-mentioned infinitesimal wires 22 having the material, properties and sizes discussed above are combined together by means of a known process to form a conductor for the electrode.

As the means for combining wires, there can be used, for example an intertwisting process, a braiding process, a winding process, etc., with the intertwisting process being the simplest of all.

Figure 4:
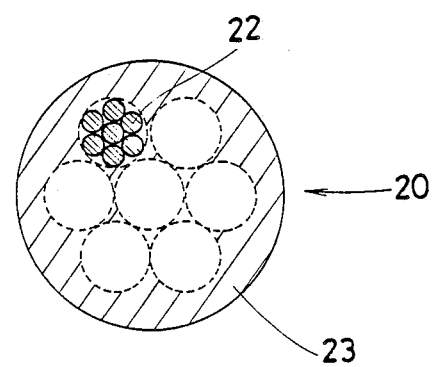
FIG. 4 is a cross-sectional view showing still another embodiment of the present invention.
Figure 3:
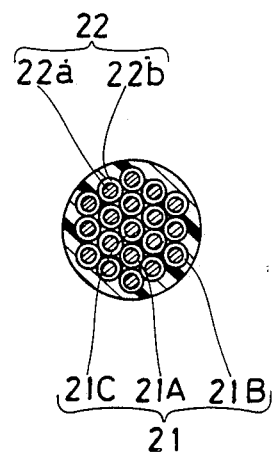
FIG. 3 is a cross-sectional view thereof.
Figure 2:
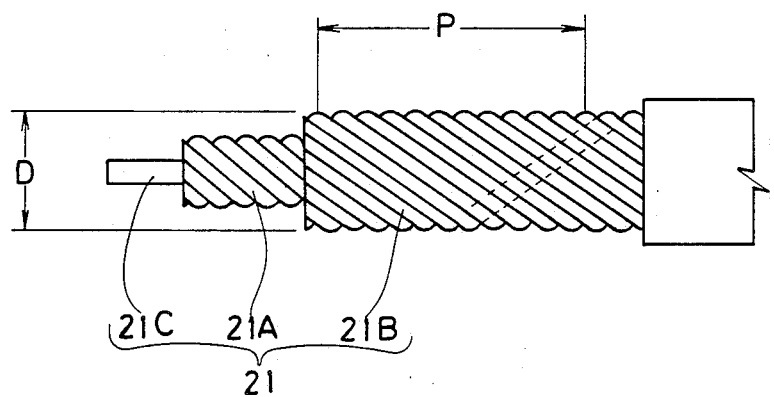
FIG. 2 is an enlarged elevational view showing another embodiment of the present invention.
Figure 5:
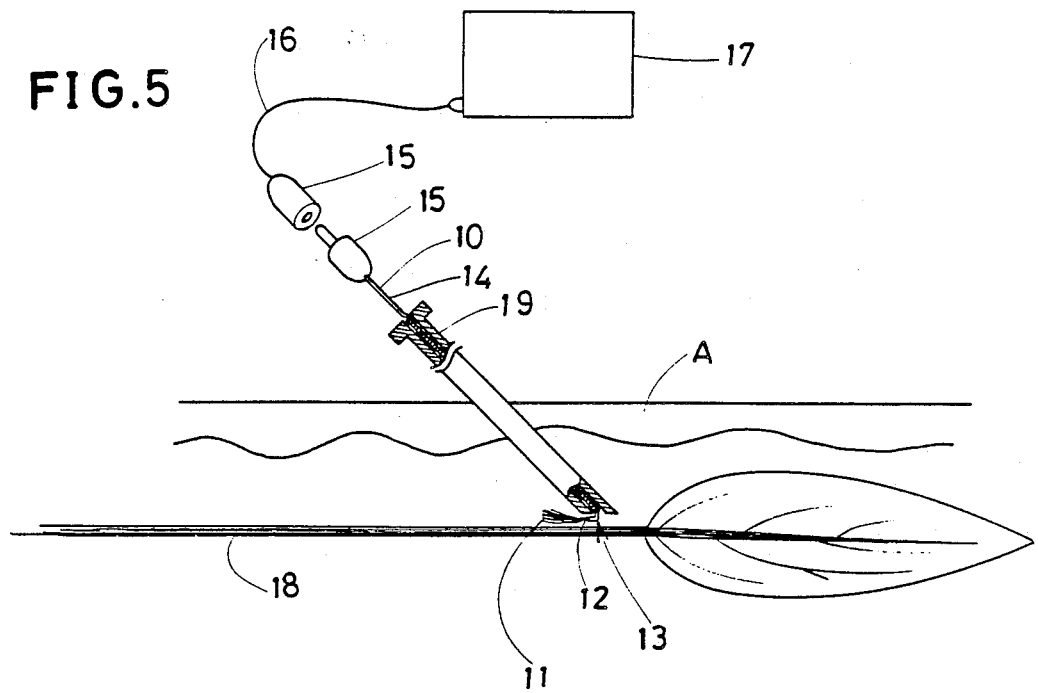
FIG. 5 is a diagrammatic view showing an example of the state of the electrode being used.

For example, in the intertwisting process, the core 21 may be formed as a strand having one layer as shown in FIG. 1 or a strand having a plural layers as shown in FIG. 2 and 3, wherein each layer is made by twisting plural infinitesimal wires 22. Furthermore, a core 21 in the shape of rope, as shown in FIG. 4, wherein plural strands are intertwisted around a center member is also contemplated by the invention. The core 21 having two or more than two layers is suitable for the electrode present invention with a viewpoint toward improving the flexbility thereof, on the condition of employing the infinitesimal wires 22. FIGS. 2 and 3 show examples of a strand-core having two layers 21A, 21B and the center member 21C which is a string of the infinitesimal wire 22 in this embodiment.

In the case of the strand-core 21, the ratio of the twisting pitch length P of the outmost layer to the outside diameter D of the core 21 is about 9–15:1, and preferably about 10–12:1. Besides, as for the strand-core 21, it is also preferable to change the direction of twist of outer layer 21B opposite to that of the inner layer 21A which are formed by intertwisting the infinitesimal wires 22. And the direction of the additional outer layers is changed, alternately opposite to that of the inner layer. The ratio P/D of the outmost layer should be maintained in the aforementioned range, whereas that of inner layers may exceed the limits.

It was confirmed by the inventors by experiment utilizing a core 21 employing infinitesimal wires 22 that the pitch length P of the twist has an effect upon flexibility, and that the core 21 becomes more flexible as the pitch length P increases. It was also ascertained that the alternate change of the twist direction from one layer to another not only prevents kinking of the electrode but also increase its flexibility, since the friction loss between the wires 22 can be reduced due to the reduced point-contact therebetween.

As an example, a core 21 having two layers, may consist of e.g. 10–25 pieces of wires 22. The first layer 21A thereof may have 4–8 pieses of wires 22 intertwisted in a direction and formed around a center member 21C having one or more layers. The second layer 21B thereof may comprise 7–15 pieces of wires 22 twisted in another direction around the first layer 21A, keeping in mind the P/D ratio.

A core 21 of this kind readily prevents such troubles as kink and snapping thereof.

The core 21 of the electrode shown in FIGS. 2 and 3 employs compound wires 22 in which the metal wire 22a is covered a coating 22b made of a resin which is compatible with the living body. In the case that such compound wires 22 are adopted for use in the core of the present invention, the flexibility of the electrode is increased, because the metal wires contact each other through the resin coating which functions as a cushion and/or lubulicant, thereby reducing the frictional loss between the wires. At the same time in the electrode, the gaps which normally exist between the bare metal wires, is filled by the resin. These wires 22 separated by resin and isolated electrically from each other are still available to individually transmit signals between devices and a plurality of positions within the living body.

The electrode 20 of the present invention is made by integrally coating the surface of the core 21 with a resin suitable for acceptance by the living body.

As a resin suitable for use in the living body, an electrical insulator having a good tissue-fitting nature within the living body and not giving rise to adverse side effects, is effective. Suitable insulators include Teflon, silicone, a fluoroplastic, or the like. A particularly desirable insulator is a high molecular weight polymer of paraxylene, such as PARILENE (trade mark: of Union Carbide Corporation). The adoption of a relatively soft resin such as silicone is suitable to raise the flexibility of the electrode 20. An example of the above-mentioned fluoroplastic, is the fluorine-containing segmented polyurethane, and the like.

The coating is achieved, for example, by use of the well known wire coating processes whereby the thickness thereof is above 30 microns. In this way, the core 21 is finished in the shape of an extremely fine thread, the diameter of which is, for example, about 0.1–0.4 mm, preferably under 0.3 mm.

In addition, in the case of the core made by intertwisting the infinitesimal wires, in order to impart the expanding/contracting property to the electrode and also to heighten the mooring effect thereof within the tissue of the living body, it is effective if the electrode is provided with spirally coiled element 24 formed continuously along the longitudinal direction thereof.

The coil diameter of the coiled portion 24 is set to be, for example, about 2-6 times the diameter of the electrode 20, that is, for example, at most 1 mm, more preferably about 0.2-0.8 mm in the present example. The inventors of this invention have confirmed by experiment that in order to make the coil diameter smaller, it is desirable to make the coiling direction opposite to the stranding direction of the core 21.

When using the electrode 20, the resin coating 23 at one end portion 13 is removed to bare the core 21, and then the end portion 13 is made to penetrate into the living body through the aid of a guide needle 19 or the like. At this time, in oder to make the piercing of the body easy and prevent the end portion thereof from shifting, it is advantageous to bend the above mentioned bared part of the core in the form of a fishing hook.

The above description is concerned only with an example of the present invention, and thus the scope of the invention is not to be so limited. This various modification and also various applications thereof can be included within the scope of the present invention.

For example, as mentioned above and as shown in FIG. 1, the core can be formed as a primary element which is made by putting together a plurality infinitesimal wires. On the other hand FIG. 4 shows the cross-section of another example of the core of the present invention wherein a secondary element is made by putting together a plurality of the above mentioned primary elements.

Further, as to the resin coat 23, in order to increase the adhesive property between the core 21 and the coat suitable for the living body, it is possible to adopt the use of a plurality of coating layers of different types of resins rather than a single coating using a resin suitable for the living body. In this case, it does not matter if the base layer is some resin other than the one used only for contacting the living body.

EXAMPLES

The following examples described in further detail several examples of the present invention.

EXAMPLE 1

The electrode of example 1 comprises: a strand core made of 19 pieces of SUS-316 stainless steel wires having a diameter and the tensile strength of 20 micron and 188 kgf/mm, respectively. The first layer has 7 pieces of the wires which are wound around a center piece of wire in the Z direction with a pitch length of 0.9 mm. The second layer has 12 pieces of wires which are twisted around the first layer in the S direction with a pitch length of 1.6 mm. A coat of Teflon resin with a thickness of 40 micron covers the core and the diameter of the electrode is 0.18 mm, wherein the core was coated after washing its surface.

The stainless steel infinitesimal wire used was obtained by stretching a wire rod of 0.08 mm in diameter through the diamond die, so that its surface was very its electrode made from these wires proved to be very supple.

EXAMPLE 2

The electrode of example 2 comprises: a strand core made of 19 pieces of compound wires in which the SUS-304 stainless steel metal wire is coated by Teflon resin with a thickness of 8 micron meter. The diameter and the tensile strength of the wire are 20 micron meter and 243 kgf/mm, respectively. The core has an inner layer and an outer layer each having a plurality of wires twisted in the S direction with a pitch length of 1.8 mm. The core is covered by a coat of Teflon with a thickness of 30 microm meter.

EXAMPLE 3

The electrode of example 3 comprises: a stranded core made of 61 pieces of the SUS-304 stainless steel wires intertwisted in the S direction and having a diameter and the tensile strength of 12 micron and 246 kgf/mm, respectively. A coating of silicone resin with thickness of 40 micron is utilized, and the diameter of the electrode is 0.19 mm, with the core being coated after washing its surface.

At this time it was recognized in cross section that the resin intruded effectively between the respective infinitesimal wires. The shearing load for the wire was in the high degree of 1,560 g. The electrode thus obtained was extremely supple.

EXAMPLE 4

The core was formed by intertwisting 3 elements each of which is first made by intertwisting 50 pieces of the same wires as used in Example 3 followed by retwisting together the above 3 elements in the S direction, and then the core is coated with Teflon resin to 40 micron in thickness.

The electrode obtained is 0.24 mm in diameter, with a shearing load 3,752 g.

Electrodes in examples 4 and 5 are made as comparative examples.

EXAMPLE 5

The electrode of example 4 comprises: a stranded core made of 7 pieces of stainless steel intertwisted wires, the diameter and the tensile strength of which are 80 micron and 83 kgf/mm, respectively. A coating of Teflon resin with a thickness of 42 micron is applied to the wires.

The shearing load of the electrode is 2,685 g.

EXAMPLE 6

The electrode of example 5 comprises: a stranded core made of 7 pieces of the SUS-304 stainless steel intertwisted wires, the diameter and the tensile strength of which are 50 microns and 65 kgf/mm, respectively. The same coating as in Example 5 as applied to the wire.

The content of Examples 1 to 6 is summarized in the following Table 1.

TABLE 1

| Example | Invention | | | | Comparative Ex. | |
|---|---|---|---|---|---|---|
| | 1 | 2 | 3 | 4 | 5 | 6 |
| Infinitesimal Wire: | | | | | | |
| Diameter (mm) | 0.02 | 0.02 | 0.012 | 0.012 | 0.08 | 0.05 |
| Tensile Strength (kgf/mm) | 188 | 243 | 246 | 246 | 83 | 65 |
| Number of Wires stranded | 19 | 19 | 61 | 150 | 7 | 7 |
| Electrode: | | | | | | |
| Diameter (mm) | 0.18 | 0.24 | 0.19 | 0.24 | 0.32 | 0.23 |
| Shearing Load (g) | 1031 | 1260 | 1560 | 3752 | 2685 | 820 |
| Judgement: | | | | | | |
| Strength (large-A, small-D) | B | A | A | A | A | D |
| Flexibility (being-A, nothing-D) | A | A | A | A | D | C |

TABLE 1-continued

| Example | Invention | | | | Comparative Ex. | |
|---|---|---|---|---|---|---|
| | 1 | 2 | 3 | 4 | 5 | 6 |
| Operating (thin-A, thick-D) | A | A | A | A | D | B |
| Synthetic Judgement (good-A, bad-D) | B | A | A | A | D | C |

RESULTS OF TREATMENT

Concerning each of these examples, the electrodes were applied in practice to living bodies with the object of restoring the functions of paralysed muscles as follows:

Result of Treatment 1

The patients included 19 persons: 13 men, and 6 women. The types of diseases were made up of 14 hemiplegics, and 5 quadriplegics.

With the consent of the patients themselves and their families, the above-mentioned electrodes of examples 1 and 2 were implanted into patients utilizing 2–38 pieces per patient, and the approxmiate electrical stimulation, the The test was prescribed at three hours a day. As the stimulation wave, there was used negative pulses with a pulse width of 0.2 ms, a stimulation frequency of 20 Hz, and with the amplitude modulated between 0 to 15 V.

In both examples, an extremely stabilized stimulation effect was obtained and no disconnection or shifting of the electrodes was observed.

Further, in the course of treatment, there was not recognized any resistance against stimulation, the nerve paley, and others; thus it was proven that our electrodes are very safe.

Result of Treatment 2

Further, about 90 pieces of the electrodes of example 1, 3, and 4 were introduced into the bodies of the patients affiliated with cerebrovascular disorders or spinal cord injury. Six patients in total were treated with the consent of the patient themselves.

In order to heighten flexibility, electrodes were used which were provided over their entire length with coiled, portions formed by coiling these original electrodes in the Z direction so that the diameter is 2.5 times the diameter of the original electrodes.

Although the electrodes have been implanted for six months, there has not been observed any disconnection or shifting of the electrodes or rejection against stimulation or an increase of resistance between the electrodes, whereby a very stable stimulation effect was secured.

In addition, the presence of the electrodes is scarcely perceptible and is not difficult for the patients to accommodate.

Result of Treatment 3

Contrary to the above results, in the comparative electrodes of example 4 which are the same as conventionally used, there occurred a high ratio of disconnection and/or the shifting of the electrodes namely 5% in the upper limbs and 50% in the lower limbs within two months after the implantation of the electrode resulting in extreme instability.

EFFECT OF THE INVENTION

As described in detail, the electrode for use in implanting into the living body according to the present invention uses as a core material extremely fine, hard stainless steel infinitesimal wires having a fitting nature and strength almost akin to the living body, so that lesions of the living body directly contacted by the infinitesimal wires is prevented and accidents to the electrode such as deformation or breakage is descreased, whereby it can be said that the electrode is high in the safety and great in effective treatment.

Because a large number of infinitesimal wires are combined together as mentioned above, the flexibility of the electrode is effectively, whereby its scope of utility is expanded.

Consequently, when the electrode is applied to certain regions or organs or to the bodies of babies and little children, whereto conventional electrodes cannot possibly be used due to physical burdens on the patients or the extent of the lesions in the tissues, the electrode of the present invention has the effect of being able to treat diseases without letting the patient experience physical disorder even at the time of implantations.

The electrode of the present invention is also useful for the living body in applications other than mere electrical stimulation use. In a word, this invention will contribute greatly to progress in medical science.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An electrode which is used as an implant for a living body which comprises
    a core member made of a plurality of infinitesimal stainless steel wires twisted into a single strand member, each of said stainless steel wires having a tensile strength greater than 180 kg/mm$^2$ and a diameter of less than 25 microns, and
    a resinous coating, compatible with the living body, provided on the surface of the core member, said electrode being in the form of a coil which is formed by closely coiling said core member provided with said resinous coating so as to have a coiling diameter of less than 0.8 mm, said coiling diameter being in the range of 2 to 6 times the diameter of the resinous coating provided on the core member, said coil having an end portion thereof which exposes the stainless steel wires for contact with said living body.

2. The electrode of claim 1, wherein the diameter of said stainless steel wires is 10 to 20 microns.

3. The electrode of claim 1, wherein said plurality of wires comprises between 7 to 200 wire members.

4. The electrode of claim 1, wherein each stainless steel wire forming the core member is individually provided with a resinous coating.

5. The electrode of claim 1 wherein the core is twisted into a strand which is coiled in the opposite direction from the coil of the resinous coating.

6. The electrode of claim 1, wherein the strand comprises a plurality of layers twisted wire members coaxially disposed with respect to each other.

* * * * *